United States Patent [19]

Mase et al.

[11] Patent Number: 4,755,274

[45] Date of Patent: * Jul. 5, 1988

[54] ELECTROCHEMICAL SENSING ELEMENT AND DEVICE INCORPORATING THE SAME

[75] Inventors: Syunzo Mase; Shigeo Soejima, both of Aichi, Japan

[73] Assignee: NGK Insulators, Ltd., Japan

[*] Notice: The portion of the term of this patent subsequent to Apr. 1, 2003 has been disclaimed.

[21] Appl. No.: 906,607

[22] Filed: Sep. 10, 1986

Related U.S. Application Data

[63] Continuation of Ser. No. 670,899, Nov. 13, 1984, abandoned.

[30] Foreign Application Priority Data

Nov. 18, 1983 [JP] Japan ............................. 58-218398
Jun. 6, 1984 [JP] Japan ............................. 59-116226

[51] Int. Cl.⁴ ............................................. G01N 27/58
[52] U.S. Cl. ................................. 204/427; 204/412; 204/425; 204/426; 204/428; 204/429
[58] Field of Search ............... 204/412, 421, 424, 425, 204/426, 427, 428, 429

[56] References Cited

U.S. PATENT DOCUMENTS

| | | | |
|---|---|---|---|
| 3,907,657 | 9/1975 | Heijne et al. | 204/406 |
| 4,272,329 | 6/1981 | Hetrick et al. | 204/412 X |
| 4,272,330 | 6/1981 | Hetrick | 204/1 T |
| 4,282,080 | 8/1981 | Muller et al. | 204/412 |
| 4,300,990 | 11/1981 | Maurer | 204/412 |
| 4,334,974 | 6/1982 | Muller | 204/424 X |
| 4,384,935 | 5/1983 | Dejong | 204/406 |
| 4,450,065 | 5/1984 | Yamada et al. | 204/412 |
| 4,498,968 | 2/1985 | Yamada et al. | 204/412 |
| 4,505,790 | 3/1985 | Mase et al. | 204/429 X |
| 4,505,804 | 3/1985 | Mase et al. | 204/429 X |
| 4,505,806 | 3/1985 | Yamada | 204/426 X |
| 4,505,807 | 3/1985 | Yamada | 204/412 X |
| 4,579,643 | 4/1986 | Mase et al. | 204/428 X |

FOREIGN PATENT DOCUMENTS

2056083 3/1981 United Kingdom .

OTHER PUBLICATIONS

European Search Report EP No. 84 30 7963—3 pages.

*Primary Examiner*—John F. Niebling
*Assistant Examiner*—Nam X. Ngwyen
*Attorney, Agent, or Firm*—Parkhurst & Oliff

[57] ABSTRACT

An electrochemical device including a sensing element of laminar structure for determining the concentration of a component of a gas, comprising a first electrochemical cell including a first solid electrolyte body, and a first and a second porous electrode disposed on the first solid electrolyte body, a second electrochemical cell including a second solid electrolyte body, and a third and a fourth porous electrode disposed on the second solid electrolyte body, and a ceramic layer having a high electric resistance and sandwiched between the first and second electrochemical cells. In another aspect of the invention, the first solid electrolyte body is porous. In this case, the first and third electrodes are exposed to substantially the same atmosphere. In either case, the first and second, or third and fourth electrodes are disposed in alignment on opposite surfaces of the first or second solid electrolyte body. In the former case, the first and second cells serve as a pumping and sensing cell, respectively. In the latter case, the first and second cells serve as a sensing and a pumping cell, respectively.

27 Claims, 15 Drawing Sheets

ELECTROCHEMICAL SENSING ELEMENT AND DEVICE INCORPORATING THE SAME

This is a continuation of application Ser. No. 670,899, filed Nov. 13, 1984, now abandoned.

BACKGROUND OF THE INVENTION

The present invention relates generally to an electrochemical device, and more particularly to a device which comprises an electrochemical sensing element including laminated electrochemical cells that use planar solid electrolyte bodies.

There have been known various electrochemical devices which use solid electrolyte bodies, for example as oxygen sensors to detect the oxygen concentration of exhaust gas from internal combustion engines of automotive vehicles. The typical examples of such oxygen sensors include an oxygen sensor which comprises a body of an oxygen-ion conductive solid electrolyte such as zirconia ceramics and which operates to determine the oxygen concentration according to the principle of an oxygen concentration cell. Also known in the art are electrochemical devices such as sensing and pumping elements for hydrogen, nitrogen, carbon dioxide, etc. In such electrochemical devices, solid electrolyte materials have been generally used in the form of a tubular body which has an elongate bore closed at its one end. In recent years, however, it has been attempted to replace the tubular solid electrolyte body with a solid electrolyte body of a planar shape, as disclosed in U.S. Pat. No. 4,334,974, in view of relatively low productivity and high cost of manufacture of solid electrolyte bodies of tubular shape, and from the standpoint of easy assembly of the parts in a planar solid electrolyte body. When such planar solid electrolyte bodies are employed, suitable electrodes are disposed in contact with the surfaces of the planar body of solid electrolyte, and the electrolyte bodies and other parts are assembled in a stacked relationship into a laminar structure constituting an electrochemical cell or sensing element.

In the art of electrochemical devices incorporating a cell of such a laminar structure using planar solid electrolyte bodies, there is also known an electrochemical element which includes an electrochemical pumping cell having pumping electrodes on opposite sides or surfaces of a planar solid electrolyte body, and an electrochemical sensing cell having sensing electrodes on another planar solid electrolyte body. Such an electrochemical element is a co-fired laminar assembly of the electrochemical pumping and sensing cells with a third planar solid electrolyte body sandwiched therebetween. The pumping cell performs a well known pumping function with a suitable voltage applied between the two pumping electrodes. In such arrangement wherein the pumping and sensing cells are constructed in a laminar structure, the voltage applied to the pumping cell may leak toward the sensing cell. This leakage affects an electromotive force generated by the sensing cell, which causes a measurement error, i.e., an erroneous output, of the electrochemical sensing element. Thus, the electrochemical element and device known in the art suffer the above indicated drawbacks.

As a modified form of such an electrochemical sensing element having two electrochemical cells, there is shown in SAE Papers 810433 and 820904 an electrochemical sensing element wherein a cavity formed between the two cells is exposed to a measurement gas outside the sensing element through a leak aperture or pin-hole having a predetermined diffusion resistance to molecules of a component of the gas to be sensed. In such a polarographic sensing element having a leak aperture through which the internal cavity communicates with the outside atmosphere, a soot or similar substance tends to be accumulated in the leak aperture, and change the diffusion resistance of the aperture. Further, the internal cavity requires to have a considerable depth. These factors lead to relatively low response characteristics of the sensing element of the polarographic type.

Further, such element is constructed from two cells combined by glass or the like having an electrical insulation layer therebetween. Such element is apt to be destroyed by a thermal stress which is generated between the glass and the solid electrolyte due to a difference in thermal expansion coefficient.

SUMMARY OF THE INVENTION

The present invention was developed in view of the aforementioned drawbacks experienced in the prior art. It is accordingly an object of the present invention to provide an electrochemical device comprising an electrochemical sensing element wherein an electromotive force generated by its sensing cell is not influenced by a pump voltage applied to its pumping cell.

Another object of the invention is the provision of such an electrochemical sensing element wherein its porous structure is protected against accumulation of soots or other substances, and which is excellent in response.

According to the present invention, there is provided an electrochemical device for determining the concentration of a component of a gaseous fluid, comprising: an electrochemical pumping cell including a first planar solid electrolyte body, and a first and a second electrode formed on the first solid electrolyte body; an electrochemical sensing cell including a second planar solid electrolyte body, and a third and fourth electrode formed on the second solid electrolyte body; and a ceramic layer having a porous structure and a high electric resistance, and sandwiched or interposed between the pumping and sensing cells, the pumping and sensing cells and the ceramic layer being co-fired into a laminar structure.

In the electrochemical device constructed as described above, the ceramic layer with a high electric resistance interposed between the pumping and sensing cells prevents a leakage flow of electric current from the pumping cell toward the sensing cell upon voltage application to the pumping cell, thereby effectively eliminating otherwise possible influence of the leakage current on the electromotive force generated by the sensing cell. Further, since the highly resistant ceramic layer between the cells is thin layer of porous structure, a thermal stress which may be generated between the ceramic layer and the planar solid electrolyte bodies due to difference in thermal expansion coefficient is held to a minimum, thereby preventing otherwise possible breakage or cracking of the solid electrolyte bodies. The electrochemical device of the invention provides the advantages indicated above.

According to another aspect of the present invention, there is also provided an electrochemical sensing element for determining the concentration of a component of a gaseous fluid, comprising: a first electrochemical cell including a first solid electrolyte body of porous structure having a predetermined diffusion resistance to molecules of said component, a first electrode of porous structure disposed on the first solid electrolyte body, and a second electrode electrically contacting the first solid electrolyte body, the first and second electrodes being spaced apart from each other;

a second electrochemical cell including a second solid electrolyte body, a third electrode of porous structure disposed on the second solid electrolyte body, and a fourth electrode disposed on said second solid electrolyte body and spaced from the third electrode; and a ceramic layer having a high electric resistance interposed between the first and second electrochemical cells, and electrically insulating at least an assembly of the first solid electrolyte body and said another solid electrolyte body, and the second solid electrolyte body, from each other, the ceramic layer cooperating with the first and second electrochemical cells to constitute a laminar structure;

the first porous electrode of the first electrochemical cell and the third porous electrode of the second electrochemical cell being exposed to substantially the same atmosphere.

In the electrochemical sensing element constructed as described above, at least the first and second solid electrolyte bodies of the two electrochemical cells used as a pumping cell and a sensing cell are electrically insulated from each other by the ceramic layer having a high electric resistance. Consequently, an electric current will not leak from the pumping cell to the sensing cell when a voltage is applied to the electrodes of the pumping cell, whereby the conventionally experienced trouble that an electromotive force to be generated by the sensing cell is influenced by such a leakage current, will be effectively eliminated.

Further, the porous structure of the first solid electrolyte body of the first electrochemical cell serves as a gas diffusion layer which contributes to reduction of variation in diffusion resistance of the solid electrolyte body due to accumulation of soot or similar substances on the solid electrolyte body. Thus, the electrochemical sensing element of this aspect of the invention suffers minimum deterioration of its operating performance.

Further, the porous structure of the first solid electrolyte body of the first electrochemical cell makes it possible to eliminate the need of forming a cavity of a relatively large depth that should be otherwise provided in the electrochemical sensing element, thereby improving response characteristics of the element.

According to another embodiment of the electrochemical device of the invention, the second electrode as well as the first electrode is a porous structure. These first and second porous electrodes are disposed in alignment with each other on opposite surfaces of the first solid electrolyte body. In this case, the first electrochemical cell serves as a pumping cell, and the second electrochemical cell serves as a sensing cell. More specifically, the electrochemical device comprises means for applying an electric current between the first and second electrodes of the pumping cell to control the atmosphere in the vicinity of the first electrode, and further comprises means for detecting an electromotive force which is generated between the third and fourth electrodes of the sensing cell.

According to a further embodiment of the electrochemical device of the invention, the fourth electrode as well as the third electrode is of a porous structure. These third and fourth porous electrodes are disposed in alignment with each other on opposite surfaces of the second solid electrolyte body. In this case, the second electrochemical cell serves as a pumping cell, and the first electrochemical cell serves as a sensing cell. More specifically, the electrochemical device comprises means for applying an electric current between the third and fourth electrodes of the pumping cell to control the atmosphere in the vicinity of the third electrode, and further comprises means for detecting an electromotive force which is generated between the first and second electrodes of the sensing cell.

BRIEF DESCRIPTION OF THE DRAWING

The foregoing and other objects, features and advantages of the present invention will become more apparent from reading the following description of preferred embodiments taken in connection with the accompanying drawing in which.

DETAILED DESCRIPTION OF THE PREFERRED EMBODIMENTS

Referring to the accompanying drawing illustrating preferred embodiments of the present invention, the arrangement of the invention will be described in detail.

Figure 1:
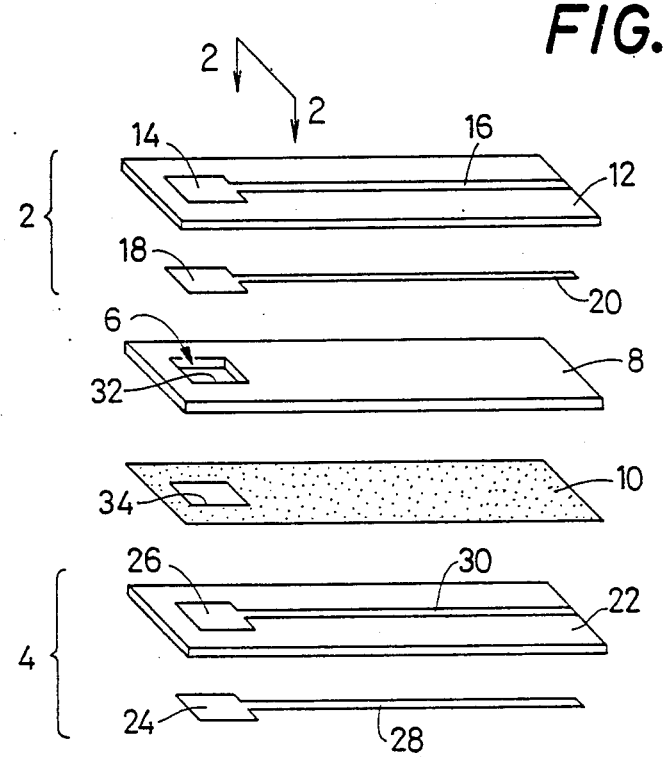
FIG. 1 is an exploded perspective view of a sensing element of one embodiment of an electrochemical device of the invention in the form of an oxygen sensor.

There is shown in the exploded perspective view of FIG. 1 a sensing element of one example of an oxygen concentration sensor which is one embodiment of an electrochemical device of the invention. The oxygen concentration sensor comprises a so-called "lean-burn sensor" which is an integral co-fired lamination of an oxygen pumping cell 2 of a laminar structure and an oxygen concentration sensing cell 4 also of a laminar structure, with a planar spacer member 8 and a thin ceramic layer 10 sandwiched therebetween. The spacer member 8 is made of a solid electrolyte material such as zirconia ceramics and has a cutout 32 defining a cavity 6. The ceramic layer 10 is of porous structure having a high electric resistance.

The pumping cell 2 includes a solid electrolyte body 12 of plate-like or planar shape made of zirconia ceramics or the like, and a porous outer pumping electrode 14 made of plantinum, for example, which is disposed on one of opposite sides or surfaces of the planar solid electrolyte body 12. More specifically, the planar solid electrolyte body 12 is provided with the outer pumping electrode 14 on its surface (outer) on the side which is exposed to an exhuast gas or other gases to be measured (hereinafter referred to as "measuring or measurement gas"). The outer pumping electrode 14 is connected to an external power source through a lead 16 extending from the electrode 14. On the other side (inner surface) of the planar solid electrolyte body 12, there is disposed an inner pumping electrode 18 which is aligned with the outer pumping electrode 14. This inner pumping electrode 18 is made of the same material as the outer pumping electrode 14, that is, made of porous platinum. The inner pumping electrode 18 is provided with a lead 20 and connected to the external power source through the lead 20.

As described above, the pumping cell 2 constitutes an electrochemical cell which comprises the planar solid electrolyte body 12, and a pair of porous pumping electrodes, i.e., the outer and inner pumping electrodes 14 and 18 disposed in contact with the outer and inner surfaces of the solid electrolyte body 12. With a DC voltage applied between these two electrodes 14 and 18, the oxygen pumping cell 2 operates in the well known manner, to introduce the oxygen in the outside measurement gas into the cavity 6 formed in the spacer member 8, or to discharge or remove the oxygen from the cavity 6 out into the outside measurement gas through the planar solid electrolyte body 12, according to the direction of flow of a DC electric current between the electrodes 14 and 18. The amounts of oxygen to be introduced and discharged are varied in proportion to the amount of current flowing the cell 2.

In the meantime, the oxygen concentration sensing cell 4 which is of the same construction as the pumping cell 2, includes a planar solid electrolyte body 22 made of zirconia ceramics or the like, and further includes an outer measuring electrode 24 and an inner measuring electrode 26 which adhere to opposite surfaces of the planar solid electrolyte body 22. Thus, an electrochemical cell in the form of an oxygen concentration sensing cell is constituted. The outer and inner measuring electrodes 24, 26 are connected, through respective leads 28, 30, to a suitable external measuring device. In the above-described arrangement of the sensing cell 4, an electromotive force due to difference in oxygen concentration is measured or detected between the outer measuring electrode 24 which is exposed to the outside measurement gas, and the inner measuring electrode 26 which is exposed to the atmosphere within the cavity 6.

The cutout 32 of the spacer member 8 is formed with substantially the same size as, and in alignment with, the inner pumping electrode 18, in order to partially define the cavity 6. Similarly, the ceramic layer 10 has a cutout 34 of substantially the same size in alignment with the cutout 32 and the inner measuring electrode 26, so that the electrodes 18, 26, and the cutouts 32, 34 cooperate to form the cavity 6.

Figure 2:
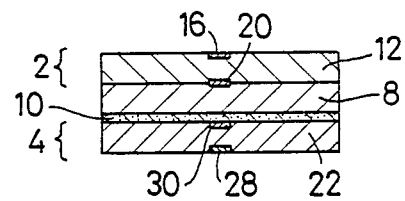
FIG. 2 is an elevational schematic view in cross section taken along line 2—2 of FIG. 1.

In the electrochemical device of the aforementioned arrangement, the thin porous ceramic layer 10 with a high electric resistance is interposed between the oxygen pumping cell 2 (including the spacer member 8) and the oxygen concentration sensing cell 4, as illustrated in FIG. 2. Therefore, the ceramic layer 10 serves to effectively block a leakage flow of an electric current from the pumping cell 2 to the sensing cell 4 when a pumping voltage is applied between the outer and inner pumping electrodes 14 and 18 to operate the pumping cell 2 for well known oxygen pumping actions. Thus, the sensing cell 4 is protected by the ceramic layer 10 from the influence of such leakage flow of current that may affect an electromotive force generated by the cell 4. Consequently, the ceramic layer 10 prevents the conventionally experienced trouble of erroneous measurement of the oxygen concentration due to variation of the electromotive force under influence of the leakage current.

Further, since the electrically insulating ceramic layer 10 between the pumping and sensing cells 2 and 4 is a thin layer of porous structure, a thermal stress which may be induced due to difference in coefficient to thermal expansion between the ceramic layer 10 and the solid electrolyte bodies 12, 22 is held to a minimum. Thus, the instant arrangement is substantially free from breakage or cracking of the solid electrolyte bodies 12, 22, and flake-off of the same.

The oxygen sensor with the foregoing arrangement and characteristics as an electrochemical device is suitably used as a lean-burn sensor for controlling an engine emitting an exhaust gas of lean air-fuel ratios whose oxygen partial pressure is higher than that of the stoichiometric air-fuel ratio.

The electrically insulating porous ceramic layer 10 between the pumping and sensing cells 2, 4 is generally a layer of ceramics which preferably comprises alumina or spinel as a major component. However, the ceramic layer 10 may be made of ceramics whose major component is selected from the group consisting of borosilicate glass, mullite, steatite, forsterite, cordierite, zircon, etc. For attaining the object of the invention with better results, the ceramic layer 10 is preferably porous and thin. The thickness of the ceramic layer 10 is generally not greater than 300 microns, preferably 5-200 microns, with the porosity ranging from about 5% to about 30%.

The oxygen sensor which has been described is manufactured in suitable known manners. For example, the electrodes 14, 18, 24, 26 and their leads, 16, 20, 28, 30 are first printed, as by a screen-printing method, on green sheets of the planar solid electrolyte bodies 12, 22. In the meantime, the ceramic layer 10 is printed, with a paste of ceramic powder, on a green sheet of the spacer member 8. Alternatively, the ceramic layer 10 may be printed on the green sheet of the solid electrolyte body 22 after the electrodes 24, 26 and leads 28, 30 have been printed. Subsequently, the green sheets of the solid electrolyte bodies 12, 22 and spacer member 8 with the printed electrodes, leads and ceramic layer 10, are superposed or stacked on each other so that the green sheet of the spacer member 8 is disposed between the two green sheets of the solid electrolyte bodies 12, 22. Finally, the superposed green sheets are co-fired, and a laminar structure of the oxygen sensor is obtained. It is possible that the ceramic layer 10 is formed on the surface of the pre-fired spacer member 8 by depositing a film of highly resistant ceramic material, by using a vacuum vapor-deposition process, sputtering process, paste-baking process, plasma spraying process, etc. In this instance, the fired spacer member 8 with the ceramic layer 10 formed thereon is sandwiched by unfired laminations of the pumping and sensing cells 2 and 4, and the laminated assembly is co-fired.

The planar solid electrolyte bodies 12 and 22, which are major or principal parts of the electrochemical pumping and sensing cells 2 and 4, may be made of aluminum nitride, $SrCeO_3$, solid solution of bismuth oxide-oxide of rare earth element, $La_{1-x}Ca_xYO_{3-\alpha}$, in place of previously indicated zirconia ceramics which is preferably used.

In the co-firing process of the electrochemical pumping and sensing cells to form an electrochemical sensing element according to the invention, it is desired that the electrodes 14, 18, 24 and 26 and their leads 16, 20, 28 and 30 are co-fired concurrently with the solid electrolyte materials 12, 8, 22. In this instance, these electrodes and leads are preferably formed by screen-printing, using as major components thereof at least one element of the platinum group including platinum, palladium, rhodium, iridium, ruthenium and osmium. The printed layers are finally fired to form the intended layers of electrodes and leads concurrently with the green sheets of the solid electrolyte bodies. In this respect, it is preferred to admix fine ceramic particles of zirconia, yttria, alumina, etc. with the materials of the electrodes and leads, for preventing flake-off and disconnection thereof. In this case, the adhesion of the electrodes and leads to the solid electrolyte bodies 12, 22 is improved.

While one preferred embodiment of the electrochemical device has been illustrated, it is understood that the invention is not limited thereto, but may be otherwise embodied, particularly with respect to the configuration of the electrochemical sensing element comprising the pumping and sensing cells. Examples of modified forms of the electrochemical sensing element are illustrated in FIGS. 3 through 10, which will be described in detail.

Figure 3:
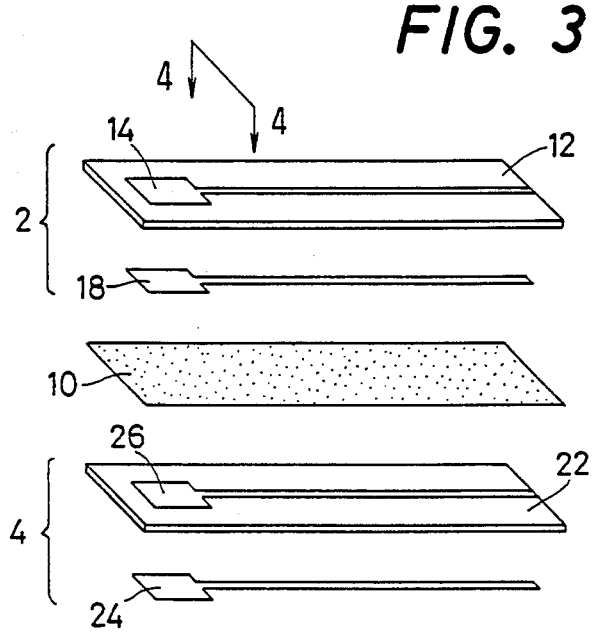
FIGS. 3, 5, 7 and 9 are exploded perspective views corresponding to FIG. 1, of other embodiments of the electrochemical device of the invention, respectively.
Figure 4:
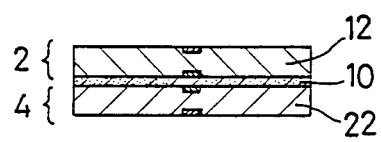
FIGS. 4, 6, 8 and 10 are elevational schematic views in cross section taken along line 4—4 of FIG. 3, line 6—6 of FIG. 5, line 8—8 of FIG. 7, and line 10—10 of FIG. 9, respectively.

An oxygen sensor shown in FIGS. 3 and 4 is not provided with such a spacer member as provided in the embodiment of FIG. 1 wherein the spacer member 8 is used. In this modified embodiment wherein only the porous ceramic layer 10 with a high electric resistance is interposed between the pumping and sensing cells 2 and 4, the porous structure of the ceramic layer 10 serves the function of the cavity 6 formed in the preceding embodiment. Thus, the ceramic layer 10 makes it possible to eliminate the spacer member 8 and thereby simplify the construction of the electrochemical device, as well as attains electric insulation between the pumping cell 2 and the sensing cell 4. In this connection, it is noted that the cavity 6 formed in the spacer member 8 and ceramic layer 10 of FIG. 1 may be filled with a porous structure of ceramics. This aspect of the invention will be referred to later in detail.

Figure 5:
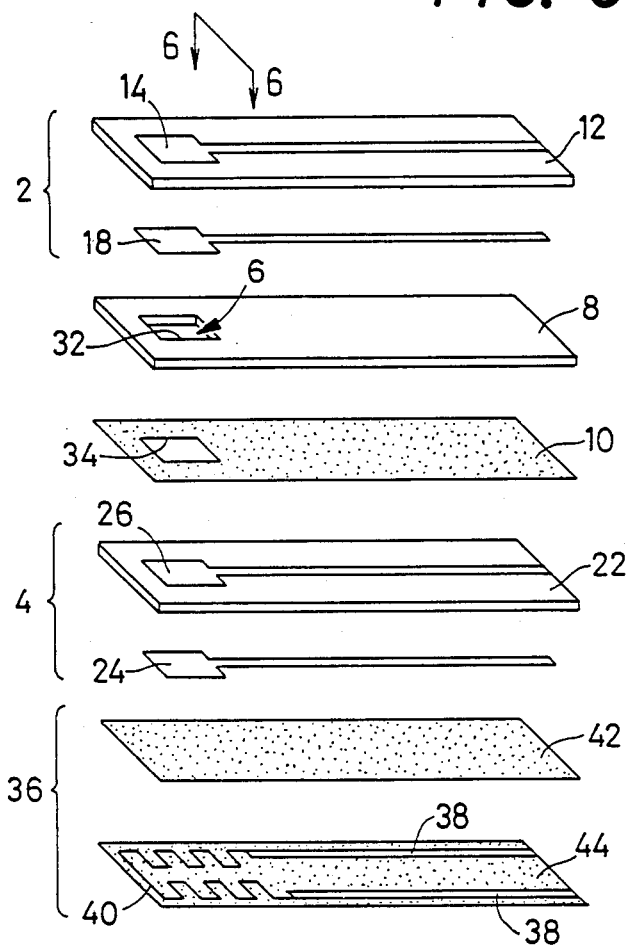
Figure 6:
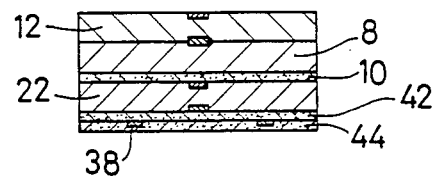

An oxygen sensor of FIGS. 5 and 6 is a modification of the preceding embodiments. That is, the distinguishing feature of the instant embodiment of FIGS. 5 and 6 is the provision of a heater 36. This heater 36 is provided to heat the solid electrolyte bodies 12 and 22 to a desired elevated temperature, in the light of the fact that the oxygen sensor is not capable of operating with sufficient reliability and accuracy while the temperature of a measurement gas such as an exhaust gas is relatively low and the temperature of the solid electrolyte bodies 12, 22 is accordingly low. The heater 36 comprises a heating element 40 which generates heat upon power application through leads 38 connected to an external power source. The heating element 40 and their leads 38 are sandwiched between an upper and a lower ceramic layer 42, 44 having a high electric resistance. The laminar structure of the heater 36 is integrally bonded to the outer side of the sensing cell 4. The ceramic layers 42 and 44 act as electrical insulators for protecting the sensing cell 4 from the influence of an electric current applied to energize the heating element 40. In this sense, it is desired that the ceramic layers 42, 44 enclosing the heating element 40 and the leads 38 are made of a material similar to that for the ceramic layer 10 disposed between the pumping and sensing cells 2 and 4. In consideration of the possibility of flake-off or other troubles due to difference in coefficient of thermal expansion, it is preferred that the ceramic layers 42, 44 are a thin layer having a porous structure.

Figure 7:
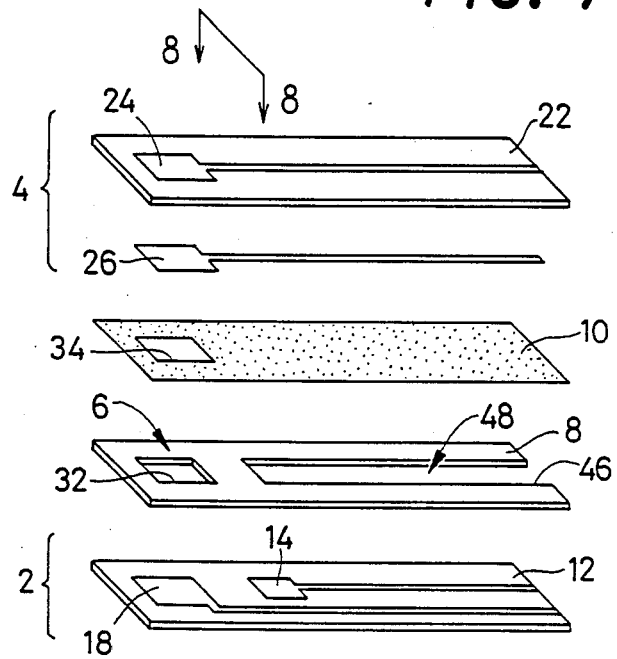
Figure 8:
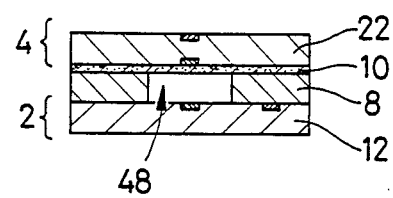

An oxygen sensor of FIGS. 7 and 8 is also used as a lean-burn sensor as in the preceding embodiments, but its pumping cell 2 employs a different structure.

Described more particularly, the pumping electrodes 14 and 18 of the pumping cell 2 are provided on the same surface of the planar solid electrolyte body 12. The pumping electrode 18 is exposed to the atmosphere in the cavity 6 partially defined by the cutout 32 formed in the spacer member 8 superposed on the solid electrolyte body 12. The spacer member 8 has an elongate cutout or recess 46, which cooperates with the solid electrolyte body 12 and the ceramic layer 10 to define a passage 48. The other electrode 14 is exposed to the atmosphere in this passage 48. In this arrangement, wherein the two pumping electrodes 14, 18 are disposed in the same plane, the application of a suitable voltage between these two electrodes 14, 18 will cause the oxygen to move in the direction along the surface of the planar solid electrolyte body 12, the amount of the oxygen to be moved being proportional to the electric current applied.

The ceramic layer 10 of this modified embodiment constructed as described above, also serves as an electrical insulator between the pumping cell 2 (including the spacer member 8) and the sensing cell 4, whereby the output of the oxygen concentration sensing cell 4 (an electromotive force generated by the cell 4) will not be affected by the voltage applied to the pumping cell 2.

Figure 9:
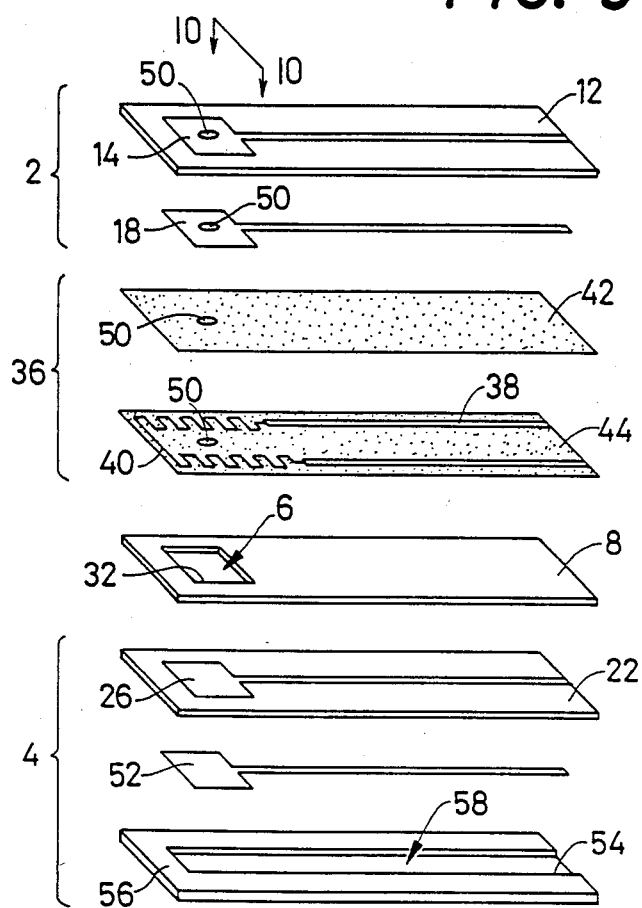
Figure 10:
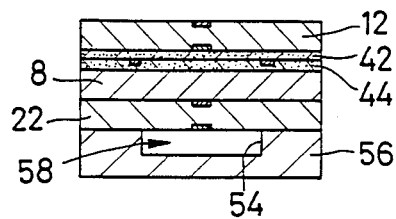

A further modified lean-burn oxygen sensor is illustrated in FIGS. 9 and 10, wherein a ventilation hole 50, i.e., a leak aperture having a predetermined diffusion resistance to molecules of a component of a measurement gas, is formed through the pumping cell 2 and the heater 36 so that the hole 50 communicates with the cavity 6 in the spacer member 8. Stated in more detail, the ventilation hole 50, which has a suitable diameter, is formed so as to extend through the thicknesses of the outer pumping electrode 14, solid electrolyte body 12, inner pumping electrolde 18, and ceramic layers 42, 44 of the heater 36. Hence, the pumping cell 2 is operated to control the amount of a component of the measurement gas, i.e., the amount of oxygen which is introduced into the cavity 6 via the ventilation hole 50.

In the embodiment of FIGS. 9 and 10, the heater 36 is interposed between the pumping cell 2 and the sensing cell 4, more precisely, between the pumping cell 2 and the spacer member 8, so that the two electrochemical cells 2 and 4 are equally heated by the heater 36. The electrically insulating or resistant ceramic layers 42, 44 of the heater 36 also serves as a porous ceramic layer with a high electric resistance for electrically insulating the pumping cell 2 from the sensing cell 4. Consequently, an otherwise required ceramic layer is eliminated, whereby the total thickness of lamination of the oxygen sensing element is accordingly reduced. The inner measuring electrode 26 of the sensing cell 4 is provided on a surface of the solid electrolyte body 22 on the side of the spacer member 8, while an outer reference electrode 52 is sandwiched between the other surface of the solid electrolyte body 22 and another planar solid electrolyte body having a cutout 54. Thus, the electrochemical oxygen sensing cell 4 is constituted.

The solid electrolyte body 56 having the cutout 54, and the solid electrolyte body 22 are laminated and cooperate to define a reference gas passage 58 which is open to the outside to introduce a reference gas, for example, the ambient atmosphere, so that the reference electrode 52 contacts the reference gas introduced in the passage 58.

While the instant oxygen sensor is adapted to introduce the measurement gas through the ventilation hole 50, unlike the previously illustrated oxygen sensors, the operation of the pumping cell 2 allows the oxygen partial pressure in the cavity 6 to be made lower than that of the actual outside measurement gas. Therefore, the instant oxygen sensor is suitably used as a lean-burn sensor, like the sensors of the preceding embodiments, for controlling an engine which emits an exhaust gas of lean air-fuel ratios whose oxygen partial pressure is higher than that of the stoichiometric air-fuel ratio.

As described above, a porous ceramic layer with a high electric resistance is provided, also in this electrochemical element of FIGS. 9 and 10, between the pumping and sensing cells 2 and 4, so that the porous ceramic layer provides the same effect and function as discussed in association with the preceding embodiments.

Referring further to FIGS. 11–22, several embodiments of an electrochemical sensing element according to another aspect of the present invention will be described in detail.

Figure 11:
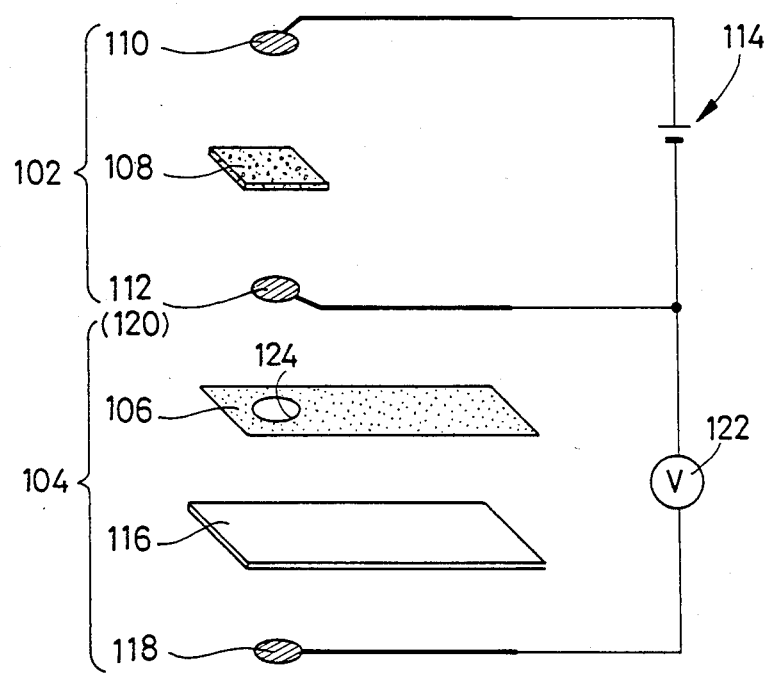
FIGS. 11-13 are exploded perspective views of basic arrangements of electrochemical device in the form of oxygen sensing elements according to another aspect of the invention.

There is shown in the exploded perspective view of FIG. 11 a basic arrangement of an oxygen concentration sensing element which is a specific form of the electrochemical sensing element of the invention. The oxygen concentration sensing element (oxygen sensor) comprises a first electrochemical cell in the form of an oxygen pumping cell 102, and a second electrochemical cell in the form of an oxygen concentration sensing cell 104, and a porous ceramic layer 106 having a high electric resistance and sandwiched between the pumping and sensing cells 102 and 104. The pumping and sensing cells 102, 104 and the porous ceramic layer 106 are laminated and co-fired into a laminar structure. The instant sensing element is one of so-called "lean-burn sensors".

The oxygen pumping cell 102 of the sensing element includes a planar ion-conductive solid electrolyte body 108 of porous structure which is made of a ceramics such as zirconia ceramics containing yttria. A porous outer pumping electrode (second electrode) 110 made, for example, of platinum and zirconia containing yttria is disposed on one of opposite sides or surfaces of the planar ion-conductive solid electrolyte body 108. More specifically, the solid electrolyte body 108 is provided with the outer pumping electrode 110 on its outer surface on the side which is exposed to an exhaust gas or other measurement gases. On the other side (inner surface) of the solid electrolyte body 108, there is disposed an inner pumping electrode (first electrode) 112 which is made of the same material as the outer pumping electrode 110, that is, made of porous platinum-zirconia.

The inner pumping electrode 112 is located in alignment with the outer pumping electrode 110. These pumping electrodes 110, 112 are connected to an external power source 114 via respective leads, so that a suitable voltage is applied between the two electrodes 110, 112.

The porous solid electrolyte body 108 of the pumping cell 102 functions as a diffusion layer having pores through which a component of a measurement gas (i.e., oxygen in this specific example) from one side of the porous solid electrolyte body 108 to the other side, with a predetermined diffusion resistance to the molecules of the component (oxygen). In this connection, it is noted that the porous solid electrolyte body 108 serves as a diffusion layer at its portion contacting the pumping electrodes 110, 112. In other words, the remaining portion of the planar solid electrolyte body 108 need not be porous, that is, may be of gastight structure. The electrochemical cell, which is constituted by the solid electrolyte body 108 and the pair of pumping electrodes 110, 112 in contact with the outer and inner surfaces of the body 108, operates in a well-known manner, upon application of a suitable voltage between the two pumping electrodes 110, 112, such that the oxygen introduced to the side of the inner pumping electrode 112 through the above indicated diffusion is pumped out toward the outer pumping electrode 110 and discharged into the outside measurement gas. The amount of flow of the oxygen to be discharged into the measurement gas is varied as a function of the amount of an electric current flowing through the cell 102.

Unlike the oxygen pumping cell 102, the oxygen concentration sensing cell 104 uses a planar gastight solid electrolyte body 116 made of zirconia ceramics containing yttria. The sensing cell 104 includes an outer reference electrode (fourth electrode) 118 which is exposed to a reference gas. The sensing cell 104 further includes an inner measuring electrode (third electrode) 120 which is exposed to the atmosphere existing in the vicinity of the inner pumping electrode 112 of the pumping cell 102. These reference and measuring electrodes 118, 120 adhere to opposite surfaces of the gastight solid electrolyte body 116 such that the electrodes 118, 120 are aligned with each other. Thus, the electrochemical cell in the form of an oxygen concentration cell is constituted. In this embodiment, the inner pumping electrode 112 also serves as the measuring electrode 120, i.e., a single electrode is commonly used as the pumping and measuring electrodes 112 and 120 of the pumping and sensing cells 102 and 104, respectively.

The measuring electrode 120 and the reference electrode 118 are connected to an external measuring device (potentiometer) 122 via respective leads. In the above-described arrangement of the sensing cell 104, an electromotive force due to a difference in oxygen concentration is measured between the reference electrode 118 exposed to the reference gas, and the measuring electrode 120 which is exposed to the atmosphere around the inner pumping electrode 112 of the pumping cell 102, which atmosphere contains the controlled amount of oxygen introduced from the outside measurement gas.

While it is required that the pumping electrodes 110 and 112 of the pumping cell 102 are disposed in aligned or opposed relation with each other, for minimizing the impedance, it is not necessarily required to align the electrodes 120 and 118 of the sensing cell 104 with each other.

The ceramic layer 106 with a high electric resistance is made of porous alumina, or highly electrically resistant ceramics as disclosed in Japanese Patent Application No. 58-239956 (laid-open under Publication No. 59-131574), and has a cutout 124 which is aligned with the inner pumping electrode 112 (measuring electrode 120). The electrode disposed within this cutout 124 functions not only as the inner pumping electrode 112 for the pumping cell 102, but also as the measuring electrode 120 for the sensing cell 104. The pumping and sensing cells 102 and 104, and the ceramic layer 106 are laminated with the ceramic layer 106 interposed between the cells 102 and 104, and concurrently fired into the electrochemical sensing element of laminar structure.

Figure 12:
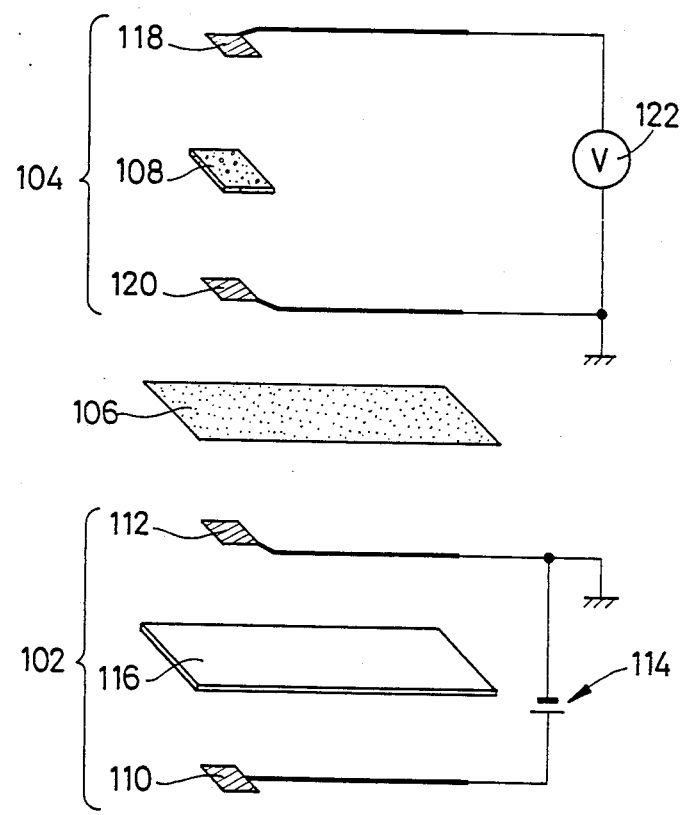

In the basic arrangement of the electrochemical sensing element illustrated in FIG. 11, a single electrode is used to serve as the inner pumping electrode 112 of the pumping cell 102, and as the measuring electrode 120 of the sensing cell 104, as previously indicated. Thus, the sensing element is simplified in construction and accordingly economically advantageous. However, it is possible that the inner pumping electrode 112 and the measuring electrode 120 are provided as two separate parts, as shown in FIG. 12. In this case of separate electrode arrangement, the operating performance of the sensing element at a relative low temperature is improved and the hysteresis is reduced.

Unlike the sensing element of FIG. 11, the sensing element of FIG. 12 uses the porous solid electrolyte body 108 for the sensing cell 104, and the gastight solid electrolyte body 116 for the pumping cell 102. Needless to say, the sensing element of this alternative arrangement functions as contemplated.

The thin porous ceramic layer 106 with a high electric resistance is interposed between the two separate inner pumping electrode 112 and the measuring electrode 120. The measuring electrode 120 is adapted to contact the atmosphere around the inner pumping electrode 112, through the porous ceramic layer 106. As it is a general practice to ground the electrodes 112 and 120, it is possible to arrange the electric connection such that their leads are connected into a single lead which is connected to the earth.

There is not always a need for providing an electrical insulator in the form of the electrically insulating porous ceramic layer 106 between the inner pumping electrode 112 and measuring electrode 120. For example, as shown in FIG. 13, it is an alternative possibility that the porous solid electrolyte body 108 and the gastight solid electrolyte body 116 are electrically insulated by a gastight ceramic layer 106 with a high electric resistance having a cutout 124 which is disposed in alignment with the electrodes 112 and 120 on opposite sides of the ceramic layer 106, and which is filled with a thin porous ceramic layer 125 made, for example, of porous zirconia, such that the opposite surfaces of the porous ceramic layer 125 is covered by the two electrodes 112 and 120.

Figure 13:
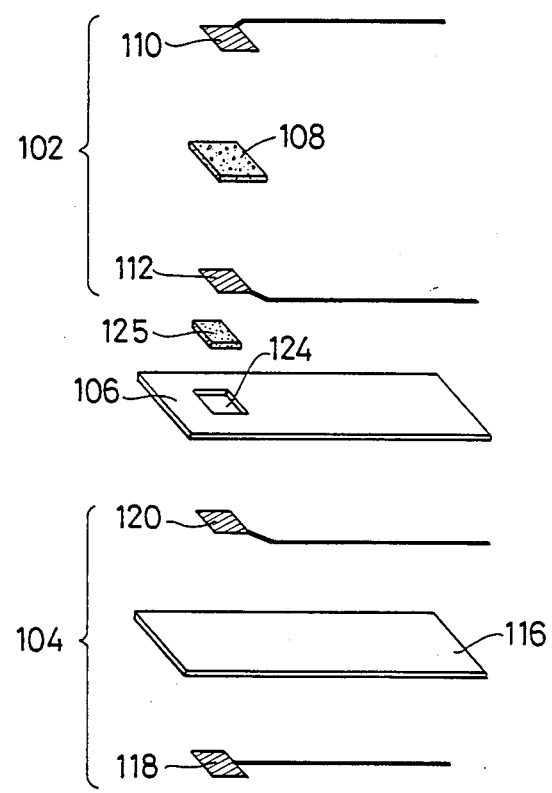

As described hitherto, the electrochemical sensing elements with the arrangements of FIGS. 11-13 employs a ceramic layer having a high electric resistance, i.e., the ceramic layer 106, interposed between the porous solid electrolyte body 108 and the gastight solid electrolyte body 116. This electrically insulating ceramic layer 106 effectively prevents a leakage current from the pumping cell 102 to the oxygen concentration sensing cell 104 during application of a predetermined pumping voltage between the inner and outer pumping electrodes 112 and 110 for operating the pumping cell 102 as an oxygen pump. As a result, the pumping voltage will exert substantially no influence on an electromotive force of the sensing cell 104, thereby eliminating the possibility of erroneous measurement or other troubles due to such a leakage current. Thus, the illustrated electrochemical sensing elements are excellent in operating accuracy in a wider range of air-fuel ratio.

Further, as shown in FIG. 11, the finely porous structure of the solid electrolyte body 108 of the pumping cell 102 functions as a diffusion layer through which the oxygen in the outside measurement gas is diffused toward the inner pumping electrode 112. This is contrary to the traditional arrangement wherein diffusion passages are provided by pin holes, a diffusion resistance of which tends to be varied by substances deposited in the holes. Further, as shown in FIGS. 11 and 12, the illustrated sensing elements demonstrate a high response thanks to the arrangement wherein the inner pumping electrode 112 and the measuring electrode 120 are positioned close to each other, or the arrangement wherein these electrodes 112, 120 are formed by a single electrode.

The oxygen partial pressure (oxygen concentration) of the atmosphere to which the measuring electrode 120 of the sensing cell 104 is exposed, is controlled by means of an oxygen pumping function of the pumping cell 102, and by way of diffusion resistance provided by the diffusion layer of the porous solid electrolyte body 108, so that the oxygen partial pressure of the measurement atmosphere around the measuring electrode 120 is made lower than that of the outside measurement gas. Consequently, the electrochemical sensing element is suitably used as a lean-burn sensor for controlling an engine which emits an exhaust gas of lean air-fuel ratios whose oxygen partial pressure is higher than that of the stoichiometric air-fuel ratio.

However, the instant electrochemical sensing element, which is suitably used as a lean-burn sensor as stated above, is also usable as an oxygen sensor for determining the oxygen concentration of an equilibrated atmosphere such as an exhaust gas whose oxygen partial pressure is substantially equal to that of the stoichiometric air-fuel ratio. Further, by reversing the direction of flow of an electric current through the pumping cell 102, the sensing element is usable as a rich-burn sensor for sensing an exhaust gas whose oxygen partial pressure is lower than that of the stoichiometric air-fuel ratio. In either case, the concentration of oxygen (a desired component) in a measurement gas, or the concentration of an excess fuel in the measurement gas is detected according to known methods of measurement.

The solid electrolyte bodies 108 and 116 may be made of suitable ceramic materials other than zirconia ceramics, which are previously indicated as the materials for the solid electrolyte bodies 8, 12, 22. As stated previously, a portion of the planar solid electrolyte body 108 adjacent to the inner pumping electrode 112 (measuring electrode 120) should serve as a diffusion layer through which the desired component of the outside measurement gas is diffused from the outer side toward the inner side of the planar solid electrolyte body 108, with a suitable diffusion resistance to the molecules of the component to be diffused. Hence, at least this portion of the planar solid electrolyte body 108 should be a porous structure having pores through the thickness of the planar solid electrolyte body 108.

The porosity of the porous structure of the planar solid electrolyte body 108 is suitably selected according to the required level of diffusion resistance. However, the optimum porosity is varied depending upon the specific process of manufacturing the porous solid electrolyte body 108. If the planar solid electrolyte body 108 is fabricated in a sintering process, the porosity is preferably held within a range of approx. 2–30% as measured according to a mercury porosimetric method (measured by Mercury Porosimeter, Type 70H made by Carlo Erba, Italy), while if the body 108 is formed in a plasma spraying process the preferred porosity range is 0.5–10% as measured with the same method.

Although the solid electrolyte body 116 is required to be more gastight than the porous solid electrolyte body 108 serving as a diffusion layer, the solid electrolyte body 116 is not necessarily completely gastight. Described differently, the solid electrolyte body 116 may be slightly porous permitting permeation of a small amount of the measurement component (oxygen) of the ambient atmosphere such as the measurement gas, to the extent that the permeated component will not give an adverse effect on the atmosphere which is diffused through the diffusion layer of the porous solid electrolyte body 108 and stays in the vicinity of the inner pumping electrode 112 (measuring electrode 120). In short, the gastight solid electrolyte body 116 may serve its intended function as long as its gastightness is not so low as to adversely affect the measuring electrode 120 and consequently the measurement of an electromotive force of the sensing cell 104.

The electrically insulating porous ceramic layer 106 disposed between the pumping and sensing cells 102 and 104 is generally a layer of ceramics which preferably comprises alumina or spinel as a major component. However, the ceramic layer 106 may be made of other ceramic materials which are previously indicated in connection with the ceramic layer 10. The ceramic layer 106, which is a layer made of such ceramic material and having a high electric resistance, is preferably porous and thin. The thickness of the ceramic layer 106 should generally be not greater than 300 microns, preferably about 5–200 microns, with the approximately porosity range of 5–30%. However, the ceramic layer 106 may be a gastight layer having a cutout as previously indicated. For example, the ceramic layer 106 may be a highly resistant gastight layer made of zirconia material having a high electric resistance as disclosed in Japanese Patent Application No. 58-239956 (laid-open under Publication No. 59-131574).

The porous ceramic layer 125 interposed between the inner pumping electrode 112 and the measuring electrode 120 as shown in FIG. 13, may be a ceramic layer having a high electric resistance, or a solid electrolyte layer, provided these layers are porous and pervious.

While the electrochemical sensing element according to the invention has a basic arrangement as illustrated in FIGS. 11–13, it is appreciated to add improvements or modifications to such a basic arrangement in various ways. Some examples of improvement and modifications are illustrated in FIGS. 14 through 19.

Figure 14:
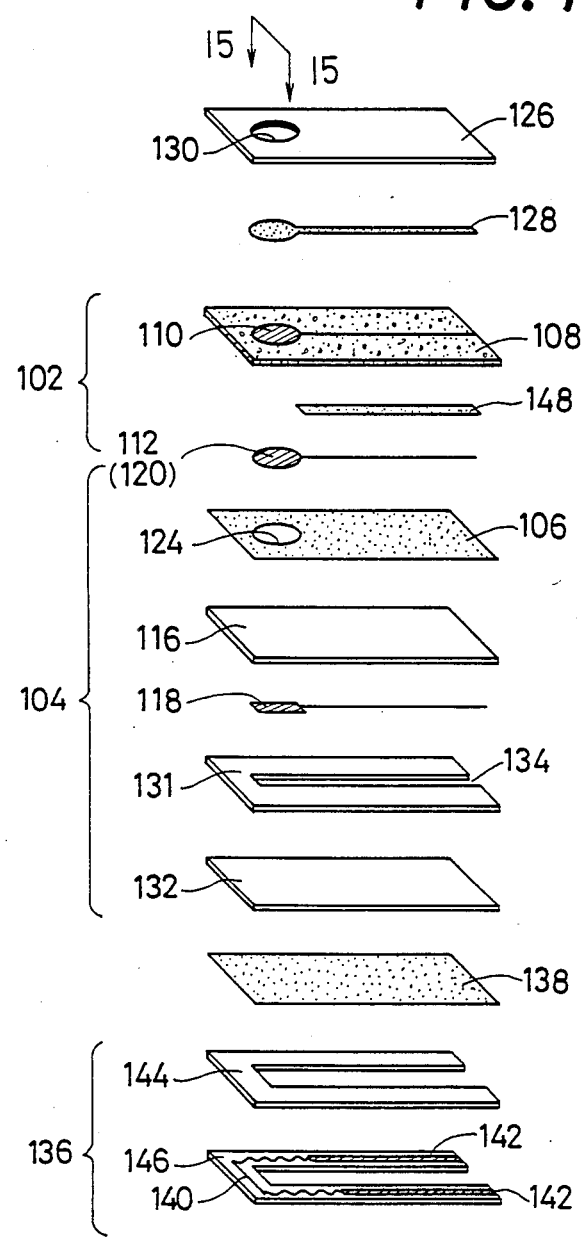
FIGS. 14, 16 and 17 are exploded perspective views of different specific forms embodying the basic arrangements of FIGS. 11-13.
Figure 15:
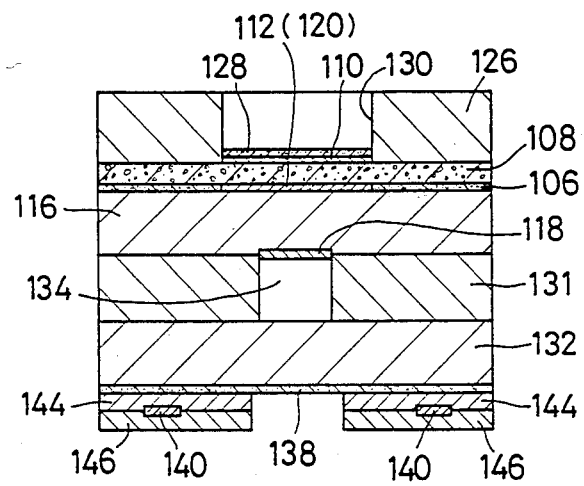
FIGS. 15 and 18 are elevational schematic views in cross section taken along line 15—15 of FIG. 14 and line 18—18 of FIG. 17, respectively.

An electrochemical sensing element of FIGS. 14 and 15 is a modification of the embodiment of FIG. 11 in which a single electrode serves commonly as the inner pumping electrode 112 and as the measuring electrode 120. That is, the embodiment of FIGS. 14 and 15 has three features that distinguish it from the embodiment of FIG. 11, as described below.

The first distinguishing feature resides in the provision of a porous alumina layer 128 formed on the surface of the porous solid electrolyte body 108 on which is formed the outer pumping electrode 110 of the pumping cell 102, and in the provision of a ceramic layer 126, on the alumina layer 128, which is a gastight structure made of zirconia or the like. The gastight ceramic layer 126 has a cutout hole 130 aligned with the outer pumping electrode 110. The outside measurement gas is introduced to the outer pumping electrode 110 through the cutout hole 130 and through the porous alumina layer 128, in a direction normal to the plane of the pumping electrode 110. Stated in more detail, the gastight ceramic layer 126 over the outer pumping electrode 110 functions as a gas-inlet layer to control the direction of entry of the outside measurement gas so that the gas is directed perpendicularly to the surface of the diffusion layer of the porous solid electrolyte body 108, that is, to prevent the measurement gas from reaching the outer pumping electrode 110 laterally on its surface. In this arrangement, the measurement gas, whose flow is oriented by the porous alumina layer 128, is diffused through the porous diffusion layer of the solid electrolyte body 108 in the direction normal to the surface thereof, whereby the gas is diffused evenly over the surface of the inner pumping electrode 112.

The second distinguishing feature of the embodiment of FIGS. 14 and 15 lies in the provision of a U-shaped spacer member 131 and a planar covering member 132 of a gastight structure which are made of zirconia or the like and laminated on the surface of the gastight solid electrolyte body 116 of the sensing cell 104 on which the reference electrode 118 is formed. The three gastight members, i.e., solid electrolyte body 116, U-shaped spacer member 131, and covering member 132 cooperate to define a reference gas passage 134 which is impervious to the measurement gas and open to the ambient atmosphere at one longitudinal end of the sensing element. The reference electrode 118 is aligned with the passage 134 and therefore exposed to the ambient atmosphere in the passage 134.

The reference electrode 118 is kept exposed to the reference gas, that is, an atmosphere of constant oxygen concentration, which results in the sensing element being usable as an oxygen sensor having a wide range of application in terms of oxygen concentration to be measured. In other words, the sensing element is capable of determining the oxygen concentration of various gases having different oxygen contents, from a fuel-rich gas, whose oxygen partial pressure is lower than that of the stoichiometric air-fuel ratio, to a fuel-lean gas, whose oxygen partial pressure is higher than that of the stoichiometric air-fuel ratio.

The third feature of the electrochemical sensing element of FIGS. 14 and 15 is the provision of a heater 136 which is disposed, via a porous insulation layer 138 of alumina or the like, on the outer surface of the covering member 132 defining the bottom of the reference gas passage 134. This heater 136 is provided to heat the solid electrolyte bodies 108, 116 to a desired elevated temperature, for improved operating performance of the sensing element while the temperature of a measurement gas such as an exhaust is relatively low and the temperatures of the bodies 108, 116 are accordingly low. The heater 136 comprises a heating element 140 which generates heat upon power application through leads 142 connected to an external power source. The heating element 140 and their leads 142 are sandwiched between a pair of gastight ceramic layers 144, 146 of zirconia or other material having a high electric resistance. The laminated structure of the heater 136 is integrally bonded to the outer side of the sensing cell 104.

The electrochemical sensing element of FIGS. 14 and 15, which is a modified form of the previously discussed basic arrangement, enjoys the same operational advantages as previously indicated, and provides further benefits accruing from the additional constructional features as discussed above. Reference numeral 148 in FIG. 14 designates an electrically resistant ceramic layer made of the same material as the ceramic layer 106, for electrically insulating the inner pumping electrode 112 (measuring electrode 120) from the planar porous solid electrolyte body 108.

Figure 16:
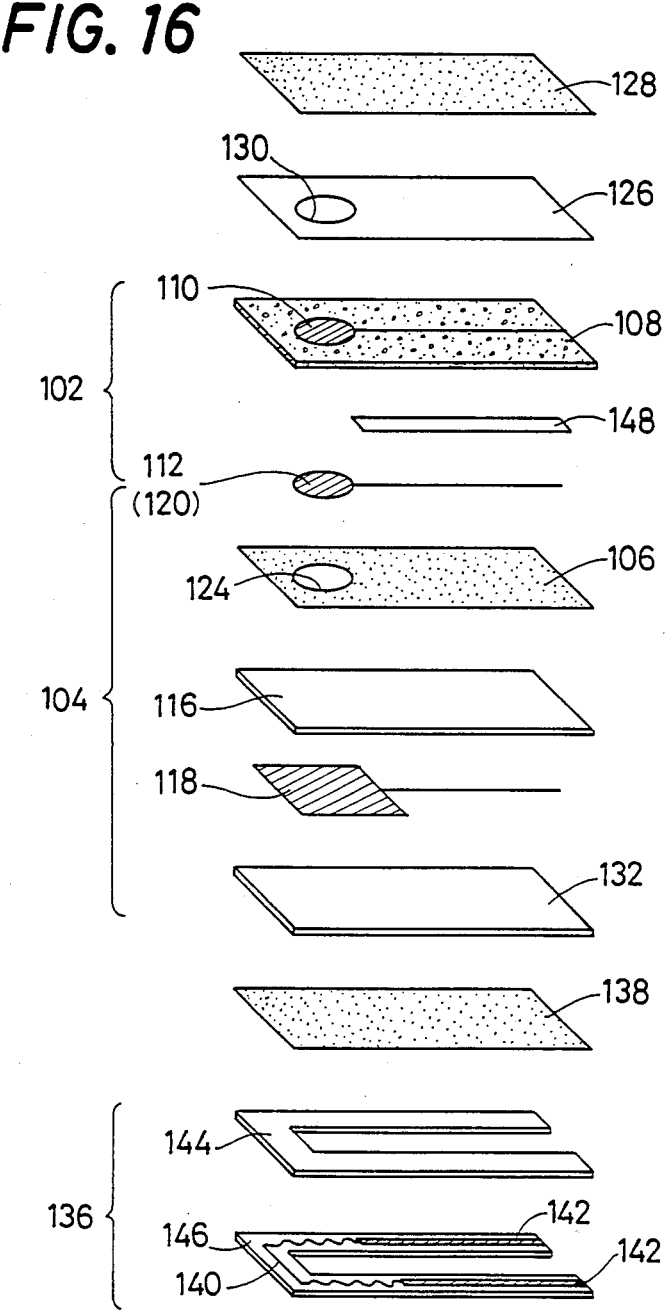

A further modified form of the electrochemical sensing element is manifested in FIG. 16, which employs the same arrangement as the embodiment of FIGS. 14 and 15, with the exception that the reference electrode 118 of the sensing cell 104 has a larger surface area and is sandwiched at its upper and lower surfaces by gastight ceramic layers, i.e., gastight solid electrolyte body 116 and gastight covering member 132.

Described more specifically, the enlargement of the surface area of the reference electrode 118 located on the side of the heater 136 contributes to increased blockage of a slight leakage current from the heater 136 to intercept such a leakage current which would otherwise influence the operation of the measuring electrode. Although the insulation layer 138 is disposed between the heater 136 and the sensing cell 104, the leakage current from the heater 136 is not completely shut off by the insulation layer 138. For this reason, the reference electrode 118 of this embodiment is enlarged for perfect elimination of the possibility that a slight amount of leaking current would reach the sensing cell 104.

The reference electrode 118, which is covered by the gastight solid electrolyte body 116 and the gastight covering member 132, is protected against exposure to the measurement gas. As is well known, an electromotive force is measured between this measuring electrode 120, and the reference electrode 118 which is held under the predetermined potential of oxygen concentration by a pumping action.

Figure 18:
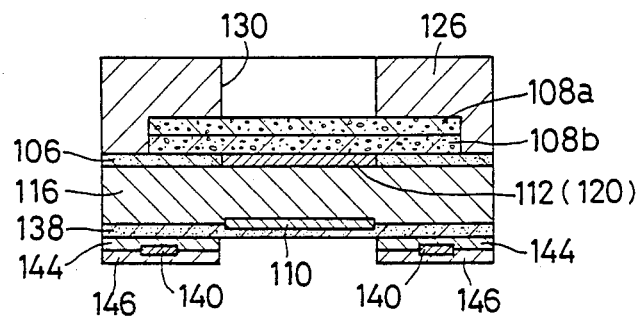
Figure 17:
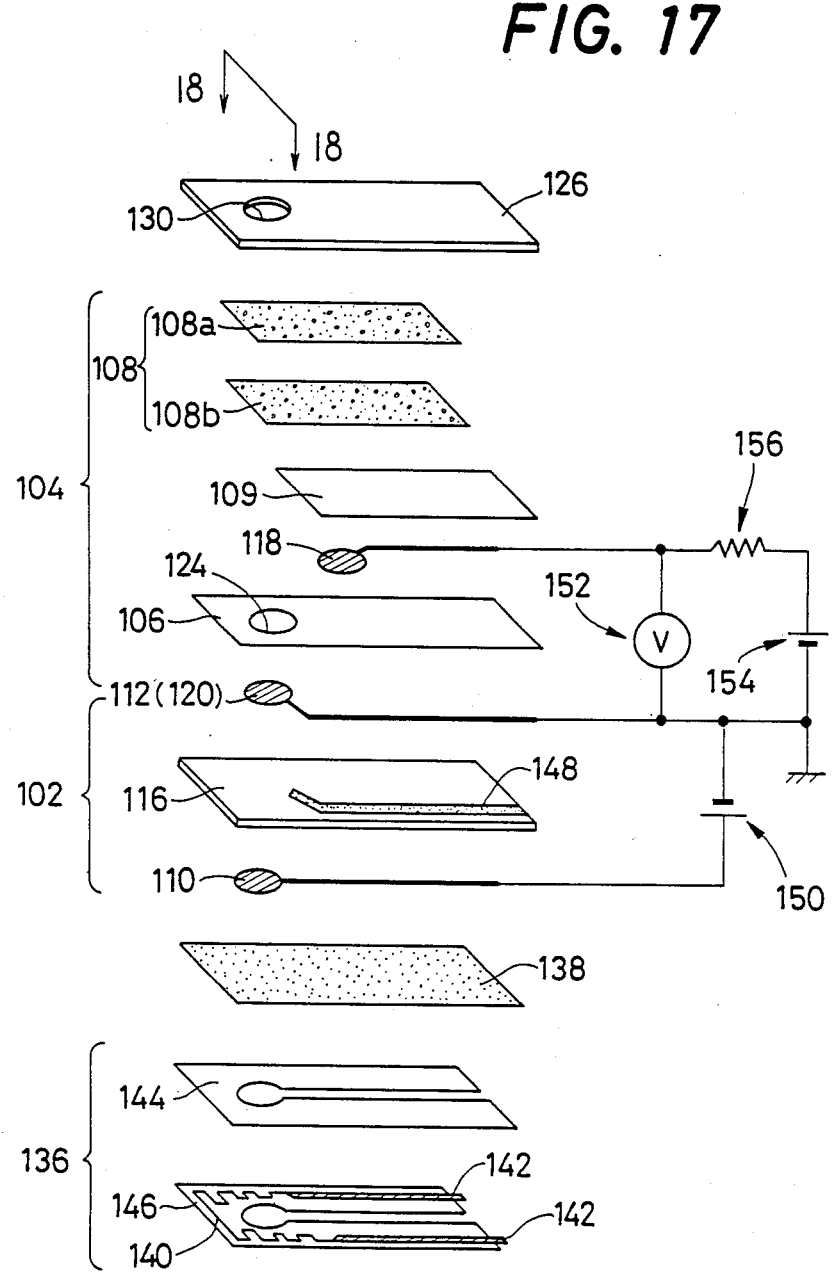

A further modified embodiment of FIGS. 17 and 18 is characterized primarily by the structure of the porous solid electrolyte body 108 of the sensing cell 104. More particularly, the solid electrolyte body 108 consists of two solid electrolyte layers 108a and 108b which have different porosities, that is, different structures of pores in the direction of diffusion of the gas. This difference in porosities between the two layers 108a, 108b of the solid electrolyte body 108 results in providing various advantages. For example, when the solid electrolyte layer 108b on the side of the inner pumping electrode 112 is given a higher porosity than the solid electrolyte layer 108a, viz., when the body 108b is made more porous than the layer 108a, the atmosphere contacting the inner pumping electrode 112 (measuring electrode 120) is made uniform, whereby the oxygen concentration sensing cell 104 can obtain increased sharpness of detection of a variation in output relative to the air-fuel ratio. On the contrary, if the porosity of the outer solid electrolyte layer 108a is made higher than that of the inner solid electrolyte layer 108b, the tendency of plugging or clogging of the pores of these porous structures is reduced. While the instant embodiment uses the two separate layers 108a, 108b whose porosities are changed in steps, it is appreciated that the outer solid electrolyte body 108 is adapted to have a porosity which is continuously varied in the thickness direction from one of its opposite surfaces to the other.

A planar solid electrolyte body 109 is a gastight layer in contact with the porous solid electrolyte body 108. As this solid electrolyte body 109 does not cover the inner pumping electrode 112, it will not affect the diffusion resistance of the solid electrolyte body 108.

In the present embodiment, as clearly shown in FIG. 18, the gastight ceramic layer 126 which controls the direction of flow of the gas into the sensing element also covers or encapsulates the lateral end faces of the porous solid electrolyte body 108 consisting of the two members 108a, 108b. Further, the gastight ceramic layer 126 is gastightly bonded to the gastight solid electrolyte body 116 of the pumping cell 102 via the electrically resistant ceramic layer 106 interposed therebetween. This arrangement permits the measurement gas to enter the pumping cell 102 only through the cutout hole 130 formed in the gastight ceramic layer 126, whereby the stream of measurement gas to be diffused through the porous solid electrolyte bodies 108a, 108b is introduced perpendicularly to the electrodes. In other words, the above arrangement eliminates otherwise possible entry of the measurement gas in the direction perpendicular to the direction of lamination of the laminar structure involved.

The reference electrode 118 of this embodiment is isolated from the measurement gas by the solid electrolyte body 109 adhering to the porous solid electrolyte body 108, and by the electrically resistant ceramic layer 106. The reference electrode 118 is powered by a power source 154 which is connected in parallel to a potentiometer 152 and in series to a resistor 156, and thus supplied with oxygen ions, whereby the reference electrode 118 is kept at a high potential of oxygen concentration.

Figure 19:
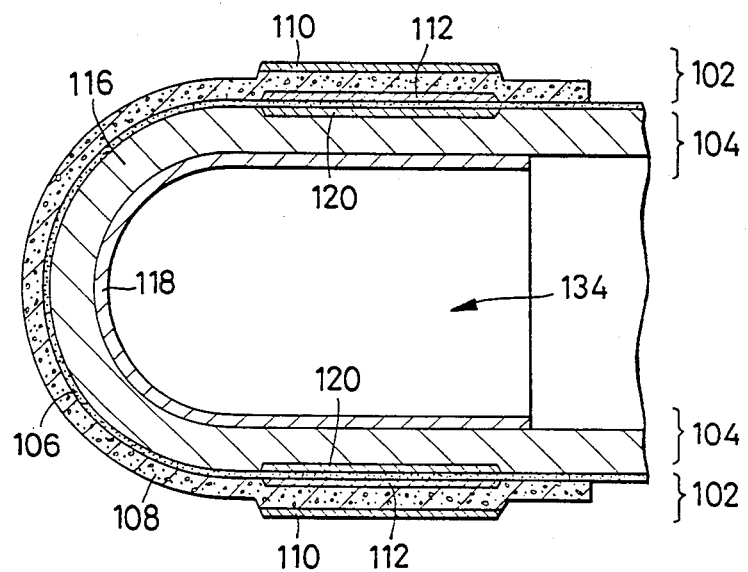
FIG. 19 is a cross sectional view of a specific example of modifications of the basic arrangements of FIGS. 11-13.

A further modified embodiment is illustrated in FIG. 19, wherein the oxygen concentration sensing cell 104 uses a tubular solid electrolyte body 116 which is closed at its one end. On the outer surface of the tubular solid electrolyte body 116, there are laminated the measuring electrode 120, ceramic layer 106 and oxygen pumping cell 102 consisting of the inner pumping eletrode 112, porous solid electrolyte body 108 and outer pumping electrode 110.

Figure 20:
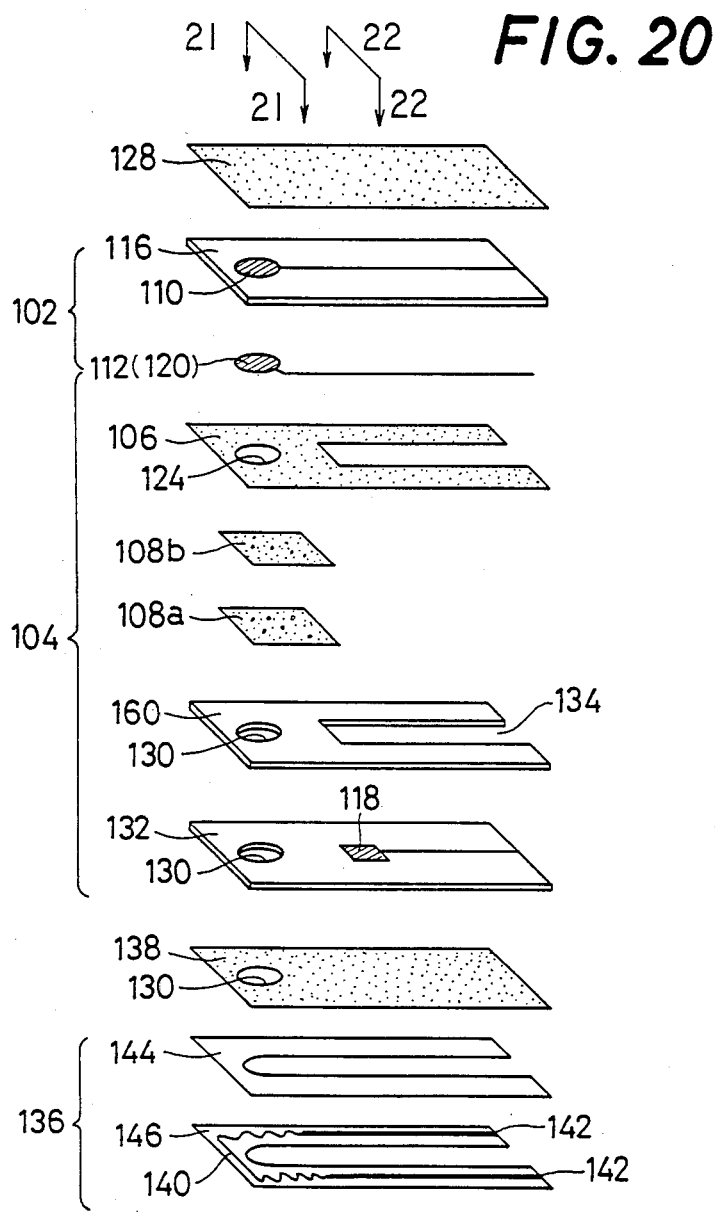
FIG. 20 is a view corresponding to FIG. 17, showing a modified form of the sensing element alternative to FIG. 17.
Figure 21:
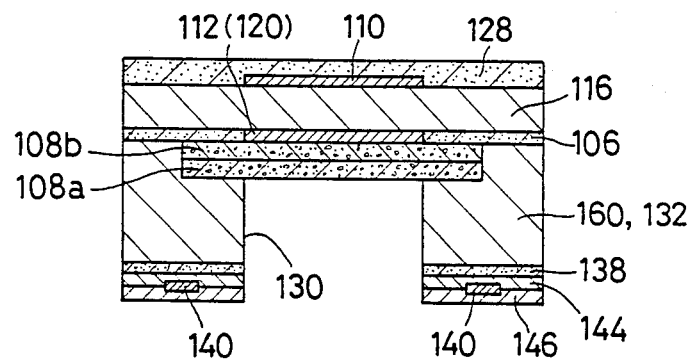
FIGS. 21 and 22 are elevational schematic views in cross section taken along lines 21—21 and 22—22 of FIG. 20, respectively.
Figure 22:
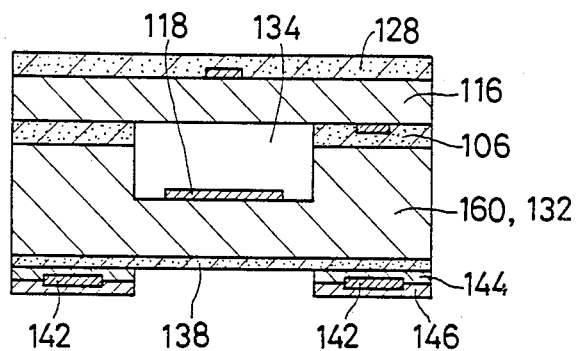

Referring further to FIGS. 20, 21 and 22, there is shown one modified form of the embodiment of FIG. 17. Unlike the sensing element of FIG. 17, this modified embodiment has a heater 136 which is disposed on the side of the sensing cell 104. The outside measurement gas is introduced through an opening formed in the heater 136, and through the cutout holes 130 formed in the sensing cell 104, and directed to the measuring electrode 120 (which also serves as the inner pumping electrode 112 of the pumping cell 102), while passing the porous structures of the two solid electrolyte layers 108a, 108b of different porosities, with a suitable diffusion resistance determined by these porosities. Further, unlike the reference electrode 118 of the embodiment of FIG. 17 which is contacted with the reference gas through electrolysis, the reference electrode 118 of this modified embodiment is contacted with the reference gas which is introduced through a reference gas passage 134 defined by a U-shaped spacer member 160 having a cutout, and by the solid electrolyte body 116 and covering member 132 that are disposed on opposite sides of the spacer member 160. The reference gas passage 134 is connected at its one end to a source of the reference gas, e.g., the ambient atmosphere, so that the reference gas having a known oxygen concentration is introduced into the passage 134 for contact with the reference electrode 118. The spacer member 160 and the covering member 132 are made of a solid electrolyte body, and cooperate with the plural solid electrolyte layers 108a, 108b to form an integral laminar assembly of solid electrolyte interposed between the reference and measuring electrodes 118, 120. This laminar assembly of solid electrolyte and the two electrodes 118, 120 constitute an electrochemical sensing cell, that is, the oxygen concentration sensing cell 104.

In the present invention, a thermal stress between the porous ceramic layer and the dense ceramic layer, which are formed into one unitary body by sintering, can be effectively eliminated, because it contains the porous ceramic layer therein.

As the other parts of the instant embodiment are functionally identical to those of the preceding embodiment, despite some difference in configuration and construction, the same reference numerals have been used to identify the corresponding parts, and a repeated detailed description thereof is omitted herein.

While the present invention has been described in its preferred forms for illustrative purpose only, the electrochemical device or sensing element of the invention is not limited to the illustrated details of constructions and arrangements; but it will be obvious to those skilled in the art that various changes, modifications and improvements may be made in the invention without departing from the spirit and scope of the invention.

Although the electrochemical device or sensing element of the invention has been illustrated and described in the form of a lean-burn or rich-burn oxygen sensor, or an oxygen sensor for determining the oxygen concentration of a measurement gas such as an exhaust gas emitted in combustion at the stoichiometric air-fuel ratio, the invention is applicable to various sensors and controllers for determining or controlling the concentration of specific components of a fluid associated with electrode reaction, such as nitrogen, carbon dioxide and hydrogen, as well as oxygen.

What is claimed is:

1. An electrochemical device for determining the concentration of a component of a gaseous fluid, comprising:
   an electrochemical pumping cell including a first planar solid electrolyte body, and a first and a second electrode formed on said first solid electrolyte body, said first solid electrolyte body comprising an oxygen ion-conducting material;
   an electrochemical sensing cell including a second planar solid electrolyte body, and a third and a fourth electrode formed on said second solid electrolyte body, said second solid electrolyte body comprising an oxygen ion-conducting material; and
   a porous electric resistive ceramic layer comprising an electric resistive ceramic material sandwiched between said pumping cell and said sensing cell, said porous electric resistive ceramic layer having a thickness of not greater than 300 microns and having a porosity which is sufficient to mitigate thermal stresses between the porous electric resistive ceramic layer and each of the solid electrolyte bodies and having substantially the same lateral and transverse dimensions to said first and second planar solid electrolyte bodies such that said porous electric resistive ceramic layer contacts both said first and second planar solid electrolyte bodies of said pumping cell and said sensing cell throughout said lateral and transverse dimensions thereof, said pumping and sensing cells and said porous electric resistive ceramic layer being co-fired into a laminar structure.

2. The electrochemical device of claim 1, wherein one of said first and second electrodes, and one of said third and fourth electrodes are exposed to a cavity which is formed between said pumping and sensing cells.

3. The electrochemical device of claim 1, wherein said porous electric resistive ceramic layer comprises alumina or spinel as a major component thereof.

4. The electrochemical device of claim 1, wherein said porous electric resistive ceramic layer has a porosity of 5–30%.

5. An electrochemical device for determining the concentration of a component of a gaseous fluid, comprising:
   a first electrochemical cell including a first solid electrolyte body of a porous structure having a diffusion resistance to the gaseous fluid, said first solid electrolyte body comprising an oxygen ion-conducting material, a first electrode of a porous structure disposed on said first solid electrolyte body, and a second electrode electrically contacting said first solid electrolyte body, said first and second electrodes being spaced apart from each other;
   a second electrochemical cell including a second solid electrolyte body, said second solid electrolyte body comprising an oxygen ion-conducting material, a third electrode of a porous structure disposed on said second solid electrolyte body, and a fourth electrode disposed on said second solid electrolyte body and spaced apart from said third electrode; and
   a porous electric resistive ceramic layer comprising an electric resistive ceramic material and being interposed between said first and second electrochemical cells, and electrically insulating at least an assembly of said first solid electrolyte body or another solid electrolyte body adhering to said first solid electrolyte body from said second solid electrolyte body, said porous electric resistive ceramic layer having a thickness of not greater than 300 microns and having a porosity which is sufficient to mitigate thermal stresses between the porous electric resistive ceramic layer and each of the solid electrolyte bodies and having substantially the same lateral and transverse dimensions to said first and second planar solid electrolyte bodies, such that said porous electric resistive ceramic layer contacts both said first and second planar solid electrolyte bodies of said first and second electrochemical cells directly, or indirectly through said another solid electrolyte body, throughout said lateral and transverse dimensions thereof, and said porous electric resistive ceramic layer cooperating with said first and second electrochemical cells to constitute a laminar structure; and
   said first electrode of said first electrochemical cell and said third electrode of said second electrochemical cell being exposed to substantially the same atmosphere.

6. The electrochemical device of claim 5, wherein said second electrode directly contacts said first solid electrolyte body.

7. The electrochemical device of claim 5, wherein said second electrode contacts said another solid electrolyte body adhering to said first solid electrolyte body.

8. The electrochemical device of claim 5, wherein said first and third electrodes are disposed in alignment with each other on opposite sides of said porous electric resistive ceramic layer.

9. The electrochemical device of claim 5, wherein said first and third electrodes are common.

10. The electrochemical device of claim 5, wherein one of said second electrode and said fourth electrodes is protected by gastight ceramic layer against exposure to said gaseous fluid, but exposed to a reference gas.

11. The electrochemical device of claim 10, wherein said gastight ceramic layers define a reference gas passage communicating with the ambient atmosphere, said one of the second and fourth electrodes being located adjacent to said reference gas passage for exposure to said ambient atmosphere.

12. The electrochemical device of claim 5, further comprising a gas-inlet layer of gastight ceramic material disposed over said first solid electrolyte body of porous structure and having a hole which is aligned with said first electrode, said hole being formed through the thickness of said gas-inlet layer, said gaseous fluid being introduced through said hole and directed to said first electrode perpendicularly to the surface of said first electrode.

13. The electrochemical device of claim 5, wherein said first solid electrolyte body consists of a plurality of solid electrolyte layers, wherein one of said solid electrolyte layers which contacts said first electrode has a porosity which is greater than the porosity in the other solid electrolyte layers.

14. The electrochemical device of claim 5, wherein said porous electric resistive ceramic layer has a porosity of 5-30%.

15. An electrochemical device for determining the concentration of a component of a gas, comprising:
a first electrochemical cell including a first solid electrolyte body of a porous structure having a diffusion resistance to the gaseous fluid, said first solid electrolyte body comprising an oxygen ion-conducting material, and a first and a second electrode of a porous structure disposed in alignment with each other on opposite surfaces of said first solid electrolyte body;
a second electrochemical cell including a second solid electrolyte body, said second solid electrolyte body comprising an oxygen ion-conducting material, a third electrode of a porous structure disposed on said second solid electrolyte body, and a fourth electrode spaced apart from said third electrode;
a porous electric resistive ceramic layer comprising an electric resistive ceramic material and being interposed between said first and second electrochemical cells, and electrically insulating at least an assembly of said first solid electrolyte body or another solid electrolyte body adhering to said first solid electrolyte body from said second solid electrolyte body, said porous electric resistive ceramic layer having a thickness of not greater than 300 microns and having a porosity which is sufficient to mitigate thermal stresses between the porous electric resistive ceramic layer and each of the solid electrolyte bodies and having substantially the same lateral and transverse dimensions to said first and second planar solid electrolyte bodies, such that said porous electric resistive ceramic layer contacts both said first and second planar solid electrolyte bodies of said first and second electrochemical cells directly, or indirectly through said another solid electrolyte body, throughout said lateral and transverse dimensions thereof, and said porous electric resistive ceramic layer cooperating with said first and second electrochemical cells to constitute a laminar structure;
said first electrode of said first electrochemical cell and said third electrode of said second electrochemical cell being exposed to substantially the same atmosphere;
means for applying an electric current between said first and second electrodes of said first electrochemical cell to control said atmosphere in the vicinity of said first electrode; and
means for detecting said atmosphere as a electromotive force which is generated between said third and fourth electrodes.

16. The electrochemical device of claim 15, wherein said first and third electrodes are disposed in alignment with each other on opposite sides of said porous electric resistive ceramic layer.

17. The electrochemical device of claim 15, wherein said first and third electrodes are common.

18. The electrochemical device of claim 15, wherein said fourth electrodes is protected by gastight ceramic layers against exposure to said gas, but exposed to a reference gas.

19. The electrochemical device of claim 18, wherein said gastight ceramic layers define a reference gas passage communicating with the ambient atmosphere, said fourth electrodes being located adjacent to said reference gas passage for exposure to said ambient atmosphere.

20. The electrochemical device of claim 15, wherein said porous electric resistive ceramic layer has a porosity of 5-30%.

21. An electrochemical device for determining the concentration of a component of a gas, comprising:
a first electrochemical cell including a first solid electrolyte body of a porous structure having a diffusion resistance to the gaseous fluid, said first solid electrolyte body comprising an oxygen ion-conducting material, a first electrode of a porous structure disposed on said first planar solid electrolyte body, and a second electrode electrically contacting said first solid electrolyte body, said first and second electrodes being spaced apart from each other;
a second electrochemical cell having a second solid electrolyte body, said second solid electrolyte body comprising an oxygen ion-conducting material, a third and a fourth electrode of a porous structure disposed in alignment with each other on opposite surfaces of said second electrolyte body;
a porous electric resistive ceramic layer comprising an electric resistive ceramic material and being interposed between said first and second electrochemical cells, and electrically insulating at least an assembly of said first solid electrolyte body or another solid electrolyte body adhering to said first solid electrolyte body from said second solid electrolyte body, said porous electric resistive ceramic layer having a thickness of not greater than 300 microns and having a porosity which is sufficient to mitigate thermal stresses between the porous electric resistive ceramic layer and each of the solid electrolyte bodies and having substantially the same lateral and transverse dimensions to said first and second planar solid electrolyte bodies, such that said porous electric resistive ceramic layer contacts both said first and second planar solid electrolyte bodies of said first and second electrochemical cells directly, or indirectly through said another solid electrolyte body, throughout said lateral and transverse dimensions thereof, and said porous electric resistive ceramic layer cooperating with said first and second electrochemical cells to constitute a laminar structure;

said first electrode of said first electrochemical cell and said third electrode of said second electrochemical cell being exposed to substantially the same atmosphere;

means for applying an electric current between said third and fourth electrodes of said second electrochemical cell to control said atmosphere in the vicinity of said third electrode; and means for detecting said atmosphere as an electromotive force which is generated between said first and second electrodes.

22. The electrochemical device of claim 21, wherein said first and third electrodes are disposed in alignment with each other on opposite sides of said porous electric resistive ceramic layer.

23. The electrochemical device of claim 21, wherein said first and third electrodes are common.

24. The electrochemical device of claim 21, wherein one of said second electrode and said fourth electrodes is protected by gastight ceramic layers against exposure to said gas, but exposed to a reference gas.

25. The electrochemical device of claim 24, wherein said gastight ceramic layers define a reference gas passage communicating with the ambient atmosphere, said second electrode being located adjacent to said reference gas passage for exposure to said ambient atmosphere.

26. The electrochemical device of claim 21, wherein said porous electric resistive ceramic layer has a porosity of 5–30%.

27. An electrochemical device for determining the concentration of a component of a gaseous fluid, comprising:

an electrochemical pumping cell including a first planar solid electrolyte body, said first planar solid electrolyte body comprising an oxygen ion-conducting material, and a first and a second electrode formed on said first solid electrolyte body;

an electrochemical sensing cell including a second planar solid electrolyte body, said second planar solid electrolyte body comprising an oxygen ion-conducting material and a third and a fourth electrode formed on said second solid electrolyte body another solid electrolyte body contacting one of said first and second planar solid electrolyte bodies, said solid electrolyte body comprising an oxygen ion-conducting material; and a porous electric resistive ceramic layer comprising an electric resistive ceramic layer and being sandwiched between said pumping cell and said sensing cell, said porous electric resistive ceramic layer having a thickness of not greater than 300 microns and having a porosity which is sufficient to mitigate thermal stresses between the porous electric resistive ceramic layer and each of the solid electrolyte bodies and having substantially the same lateral and transverse dimensions to said first and second planar solid electrolyte bodies such that said porous electric resistive ceramic layer contacts said one of the first and second planar solid electrolyte bodies of said pumping cell and said sensing cell indirectly through said another solid electrolyte body, and directly contacts the other of said first and second planar solid electrolyte bodies throughout said lateral and transverse dimensions thereof, said pumping and sensing cells and said porous electric resistive ceramic layer being co-fired into a laminar structure.

* * * * *